United States Patent
Nasrollahzadeh Abyazani et al.

(10) Patent No.: US 10,406,114 B2
(45) Date of Patent: Sep. 10, 2019

(54) ANTIBIOTIC-LOADED TRANSDERMAL PATCH

(71) Applicants: Masoumeh Nasrollahzadeh Abyazani, Tehran (IR); Fariba Ganji, Tehran (IR); Seyed Mojtaba Taghizadeh, Tehran (IR); Ebrahim Vasheghani Farahani, Tehran (IR)

(72) Inventors: Masoumeh Nasrollahzadeh Abyazani, Tehran (IR); Fariba Ganji, Tehran (IR); Seyed Mojtaba Taghizadeh, Tehran (IR); Ebrahim Vasheghani Farahani, Tehran (IR)

(*) Notice: Subject to any disclaimer, the term of this patent is extended or adjusted under 35 U.S.C. 154(b) by 0 days.

(21) Appl. No.: 16/004,352

(22) Filed: Jun. 9, 2018

(65) Prior Publication Data
US 2018/0289629 A1 Oct. 11, 2018

Related U.S. Application Data

(60) Provisional application No. 62/517,932, filed on Jun. 11, 2017.

(51) Int. Cl.
- A61K 9/70 (2006.01)
- A61K 47/32 (2006.01)
- A61K 31/545 (2006.01)
- A61K 9/51 (2006.01)

(52) U.S. Cl.
CPC .......... *A61K 9/7038* (2013.01); *A61K 9/7053* (2013.01); *A61K 31/545* (2013.01); *A61K 47/32* (2013.01); *A61K 9/5123* (2013.01)

(58) Field of Classification Search
None
See application file for complete search history.

(56) References Cited

U.S. PATENT DOCUMENTS

| | | | |
|---|---|---|---|
| 3,734,097 A | 5/1973 | Zaffaroni | |
| 5,508,038 A * | 4/1996 | Wang | A61K 9/7053 424/448 |
| 6,231,885 B1 * | 5/2001 | Carrara | A61K 9/7061 424/448 |
| 2006/0222716 A1 * | 10/2006 | Schwarz | A61K 9/5123 424/489 |
| 2008/0085301 A1 | 4/2008 | Lane | |

OTHER PUBLICATIONS

Nasrollahzadek, Development and Optimization of Cephalexin-Loaded Solid Lipid Nanoparticles Using D-Optimal Design. Advanced Science, Engineering, Medicine. 2016;vol. 8, issue 9, pp. 695-704.

* cited by examiner

*Primary Examiner* — Carlos A Azpuru
*Assistant Examiner* — Casey S Hagopian
(74) *Attorney, Agent, or Firm* — Bajwa IP Law Firm; Haris Zaheer Bajwa

(57) ABSTRACT

A method for producing an antibiotic-loaded transdermal patch including preparing a polymeric adhesive solution by dissolving a polymeric mixture in a solvent, preparing a plurality of antibiotic-loaded solid lipid nanoparticles (SLNs), forming a patch formulation by mixing the plurality of antibiotic-loaded SLNs and the polymeric adhesive solution, and forming a layer of the patch formulation on a substrate.

12 Claims, 9 Drawing Sheets

ANTIBIOTIC-LOADED TRANSDERMAL PATCH

CROSS-REFERENCE TO RELATED APPLICATION

This application claims the benefit of priority from U.S. Provisional Patent Application Ser. No. 62/517,932, filed on Jun. 11, 2017, and entitled "PRESSURE SENSITIVE ADHESIVE PATCH CONTAINING ANTIBIOTIC-LOADED SOLID LIPID NANOPARTICLES," which is incorporated herein by reference in its entirety.

TECHNICAL FIELD

The present disclosure generally relates to transdermal patches, particularly to antibiotic-loaded transdermal patches, more particularly to a method for producing antibiotic-loaded transdermal patches.

BACKGROUND

Irregular use of antibiotics has been known to cause an increase to antimicrobial resistance. Due to the fact that the resistance of bacteria to antibiotics continues and the amount of effective and available antibiotics reduces, the spread rate of infectious diseases will be increased. In addition to the antibiotic resistance, there are other adverse effects of antibiotics such as nausea, vomiting, diarrhea, and skin allergies.

In some situations, antibiotics may be recommended as part of a prophylaxis regimen, so decreasing the amount of prescribed antibiotic in these situations can be helpful for avoiding the adverse effects of the antibiotics. One of the non-acute situations may be surgical antibiotic prophylaxis which accounts for about 30% to 50% of all prescribed antibiotics for preventing postoperative wound infections. One strategy for reducing the amount of administered antibiotic and related side effects can be the application of antibiotic-loaded patches as transdermal drug delivery system for treating infected or surgical areas locally.

Although transdermal patches have certain advantages like minimized drug metabolism in liver or gastrointestinal tract, they have several shortcomings such as low skin impermeability and low loading capacity for drugs with high required dose such as antibiotics. Accordingly, there is a need for a transdermal patch for antibiotic delivery with high loading capacity and high antimicrobial activity. Moreover, there is a need for an antibiotic-loaded transdermal patch with high loading capacity for antibiotics with 200 mg/day required dose and with high skin penetration for the antibiotics.

SUMMARY

This summary is intended to provide an overview of the subject matter of the exemplary embodiments of the present disclosure, and is not intended to identify essential elements or key elements of the subject matter, nor is it intended to be used to determine the scope of the claimed implementations. The proper scope of the exemplary embodiments of the present disclosure may be ascertained from the claims set forth below in view of the detailed description below and the drawings.

In one general aspect, the present disclosure describes an exemplary method for producing an antibiotic-loaded transdermal patch. The exemplary method may include preparing a polymeric adhesive solution by dissolving a polymeric mixture in a solvent, preparing a plurality of antibiotic-loaded solid lipid nanoparticles (SLNs), forming a patch formulation by mixing the plurality of antibiotic-loaded SLNs and the polymeric adhesive solution, and forming a layer of the patch formulation on a substrate.

The above general aspect may include one or more of the following features. In some exemplary implementations, preparing the polymeric adhesive solution by dissolving the polymeric mixture in the solvent may include the polymeric mixture of one of acrylic-based polymers, polyisobutylene (PIB)-based polymers, and silicon-based polymers, or combinations thereof. In some exemplary embodiments, the PIB-based polymers may include low-molecular-weight (LMW) PIB and high-molecular-weight (HMW) PIB with a ratio of LMW PIB/HMW PIB between about 70:30 and about 60:40.

According to some exemplary embodiments, the plurality of antibiotic-loaded SLNs may include an antibiotic, a lipid base, a surfactant, a cosurfactant, zeta-potential adjusting salt, or combinations thereof. In some exemplary embodiments, the plurality of antibiotic-loaded SLNs may have a diameter between 90 nm and 180 nm. In some exemplary embodiments, the plurality of antibiotic-loaded SLNs may include the antibiotic with a molar mass less than about 500 g/mol. In some exemplary embodiments, the lipid base may include one of solid α-tocopherol succinate, triglycerides, partial glycerides, fatty acids, steroids, waxes, or combinations thereof.

According to some exemplary embodiments, the patch formulation may include the plurality of antibiotic-loaded SLNs with a concentration between about 3% and about 13% of the weight of the patch formulation. In some exemplary embodiments, the patch formulation may further include free antibiotic and penetration enhancer. In some exemplary embodiments, the patch formulation may include free antibiotic with a concentration between about 7% and about 10% of the weight of the patch formulation. In some exemplary embodiments, the patch formulation may include the penetration enhancer with a concentration less than about 10% of the weight of the patch formulation. In some exemplary embodiments, the penetration enhancer may include one of blank SLNs, oleic acids, or combinations thereof. In some exemplary embodiments, the layer of the patch formulation may have a thickness between about 60 μm and about 140 μm.

In another general aspect, the present disclosure describes an exemplary antibiotic-loaded transdermal patch including a layer of a patch formulation coated on a substrate. The patch formulation may include a plurality of antibiotic-loaded solid lipid nanoparticles (SLNs) with a concentration between about 3% and about 13% of the weight of the patch formulation dispersed in a polymeric adhesive solution and free antibiotic.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

Figure 1A:
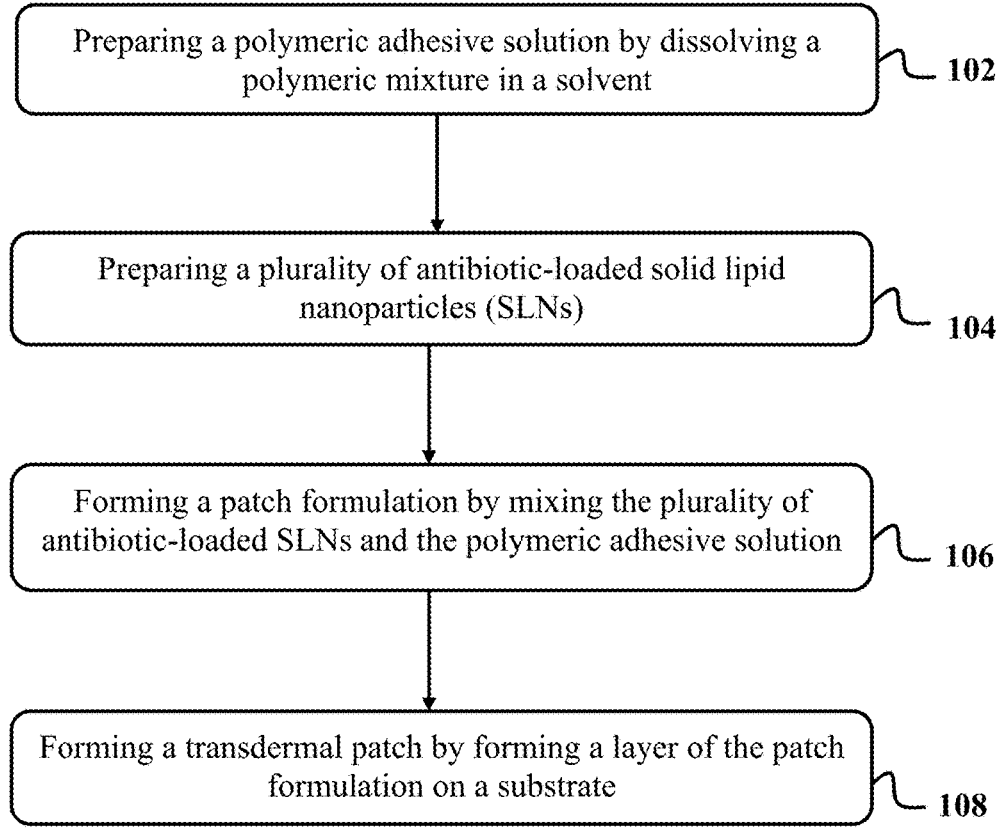
FIG. 1A illustrates an exemplary method for preparing an antibiotic-loaded transdermal patch, consistent with one or more exemplary embodiments of the present disclosure.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown but is to be accorded the widest possible scope consistent with the principles and features disclosed herein.

Transdermal patches as a delivery system for antibiotics may prevent wound infections and may aid in decreasing unnecessary administration of the antibiotics. However, low drug loading may be an obstacle for designing antibiotic-loaded transdermal patches. High amounts of the drug in transdermal patches diminishes adhesiveness of the transdermal patch and leads to burst drug release. Therefore, one of the criteria to design a transdermal patch may be the daily dosage of drug agent which should be lower than 100 mg/day, while antibiotic daily dosage may be more than about 200 mg for adults.

Nanoparticles such as solid lipid nanoparticles (SLNs) are engineered nanostructures that may efficiently encapsulate the antibiotics with high physical and chemical stability and high loading capacity. The SLNs being utilized as a drug reservoir and a penetration enhancer may entrap the antibiotics inside a lipid matrix of the SLNs which prevents antibiotics from oxidative reactions and may facilitate penetration of the antibiotics through the skin.

In order to overcome above mentioned shortcomings of the transdermal patches, disclosed herein is an exemplary antibiotic-loaded transdermal patch including a plurality of antibiotic-loaded SLNs to increase drug loading and drug penetration through the skin. The advantages of SLNs are that they may enhance the therapeutic effect of the transdermal patch by protecting the antibiotics from enzymatic degradation, preventing transepidermal water loss, fast drug penetration, and releasing the antibiotics in a controlled manner for prolonged periods.

Disclosed herein is an exemplary method for producing an antibiotic-loaded transdermal patch for antibiotic prophylaxis to prevent wound infection and decrease unnecessary antibiotic administration. The antibiotic-loaded transdermal patch may be used for local and systemic delivery of the antibiotics through skin for a sustained period of time.

The exemplary antibiotic-loaded transdermal patch of the present disclosure may include the plurality of antibiotic-loaded SLNs dispersed within an adhesive matrix of the antibiotic-loaded transdermal patch. In some exemplary embodiments, the exemplary antibiotic-loaded transdermal patch may need a lower amount of the antibiotic relative to oral antibiotic prophylaxis.

FIG. 1 shows method 100 for producing the antibiotic-loaded transdermal patch, consistent with one or more exemplary embodiments of the present disclosure. Method 100 may include preparing a polymeric adhesive solution by dissolving a polymeric mixture in a solvent (step 102), preparing a plurality of antibiotic-loaded solid lipid nanoparticle (SLNs) (step 104), forming a patch formulation by mixing the plurality of antibiotic-loaded SLNs and the polymeric adhesive solution (step 106), and forming a layer of the patch formulation on a substrate (step 108).

Step 102 may include preparing the polymeric adhesive solution by dissolving the polymeric mixture in the solvent. In some exemplary embodiments, the polymeric mixture may include one of the acrylic-based polymers, polyisobutylene-based polymers, and silicon-based polymers, or combinations thereof. In some exemplary embodiments, the polymeric mixture may include at least one low-molecular-weight (LMW) polymer and at least one high-molecular-weight (HMW) polymer.

In some exemplary embodiments, the polymeric mixture may include the LMW polymer and the HMW polymer with a ratio between 70:30 and 60:40 (LMW polymer:HMW polymer). In one or more exemplary embodiments, the low molecular weight polymers may have a molecular weight between about 40000 g/mol and about 120000 g/mol. In one or more exemplary embodiments, the high molecular weight polymers may have a molecular weight between about 500000 g/mol and about 1100000 g/mol.

In some exemplary embodiments, using the polymeric mixture including polymers with different molecular weights may increase the loading capacity of the antibiotic-loaded transdermal patch while maintaining adhesiveness of the antibiotic-loaded transdermal patch at an acceptable or desired level.

In some exemplary embodiments, dissolving the polymeric mixture in the solvent may include dissolving the polymeric mixture in one of toluene, n-hexane, cyclohexane, or combinations thereof. In some exemplary embodiments, dissolving the polymeric mixture in the solvent may include dissolving the polymeric mixture in the solvent at room temperature overnight. In one or more exemplary embodiments, dissolving the polymeric mixture in the solvent may include dissolving the polymeric mixture in the solvent using one of a rotary mixer or a mechanical mixer.

Step 104 may include preparing the plurality of antibiotic-loaded SLNs. In some exemplary implementations, preparing the plurality of antibiotic-loaded SLNs may include using one of water-in-oil (W/O) nanoemulsion, oil-in-water (O/W) nanoemulsion, ultrasonication, micro fluidization, high-pressure homogenization, water-in-oil-in-water (W/O/W) double emulsion, solvent emulsification/evaporation, diffusion, or combinations thereof.

Figure 1B:
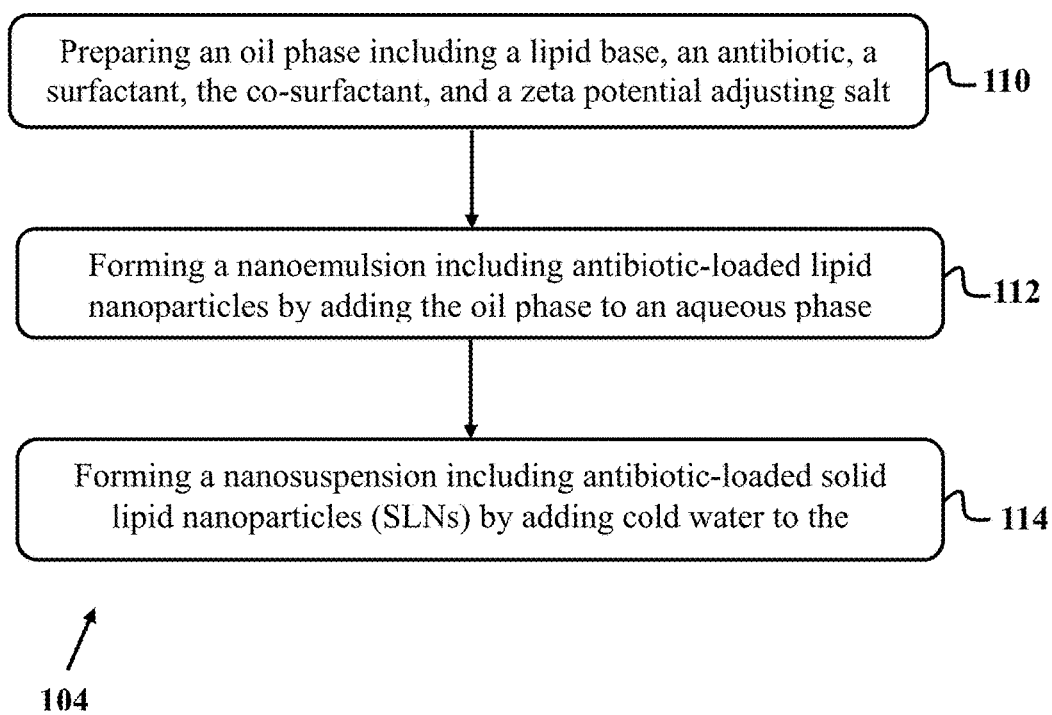
FIG. 1B illustrates an exemplary method for preparing the plurality of antibiotic-loaded SLNs using the oil-in-water (O/W) method, consistent with one or more exemplary embodiments of the present disclosure.

FIG. 1B shows an exemplary implementation of step 104 for preparing the plurality of antibiotic-loaded SLNs using the O/W method, consistent with an exemplary embodiment of the present disclosure. Preparing the plurality of antibiotic-loaded SLNs using the O/W method may include preparing an oil phase including a lipid base, an antibiotic, a surfactant, a cosurfactant, and a zeta potential adjusting salt (step 110), forming a nanoemulsion including antibiotic-loaded lipid nanoparticles by adding the oil phase to an aqueous phase (step 112), and forming a nanosuspension including cephalexin-loaded SLNs by adding cold deionized water to the nanoemulsion (step 114).

Step 110 may include preparing the oil phase including the lipid base, the antibiotic, the surfactant, the cosurfactant, and the zeta potential adjusting salt. In one or more exemplary embodiments, the oil phase may be prepared by heating a mixture of the lipid base, the antibiotic, the surfactant, the cosurfactant, and the zeta potential adjusting salt to a temperature of a melting point of lipids. In an exemplary embodiment, the oil phase may be heated to a temperature between about 70° C. and about 80° C. In some exemplary embodiments, the oil phase may be stirred at a speed of about 2000 round per minute (RPM) for a time period of about 10 minutes to obtain a homogeneous oil phase.

In one or more exemplary embodiments, the antibiotic may include antibiotics with molar mass less than about 500 g/mol. In an exemplary embodiment, the antibiotic may include one of cephalosporin, aminoglycoside, carbapenem, lincosamide, monobactam, penicillin, quinolone, tetracyclines, or combinations thereof.

In some exemplary embodiments, cephalosporin may include one of cefacetrile, cefadroxil, cefalexin, cefaloglycin, cefalonium, cefaloridine, cefalotin, cefapirin, cefatrizine, cefazaflur, cefazedone, cefazolin, cefradine, cefroxadine, ceftezole, cefaclor, cefprozil, cefuroxime, cefmetazole, cefoxitin, cefcapene, cefdaloxime, cefdinir, cefditoren, cefetamet, cefixime, cefotaxime, cefovecin, cefpodoxime, ceftamere, ceftibuten, ceftizoxime, cefepime, or combinations thereof. In some exemplary embodiments, aminoglycosides may include one of gentamicin, kanamycin, netilmicin, tobramycin, or combinations thereof.

In some exemplary embodiments, carbapenem may include one of meropenem, ertapenem, or combinations thereof. In some exemplary embodiments, lincosamide may include clindamycin. In some exemplary embodiments, monobactam may include aztreonam. In some exemplary embodiments, penicillin may include one of amoxicillin, ampicillin, flucloxacillin, methicillin, oxacillin, penicillin G, or combinations thereof. In some exemplary embodiments, quinolone may include ciprofloxacin. In some exemplary embodiments, sulfonamide may include mafenide, sulfanilamides, or combinations thereof.

In some exemplary embodiments, antibiotic to lipid base ratio may be between about 10% and about 40%. In some exemplary embodiments, the lipid base may include a lipid base with a melting point higher than 60° C. In some exemplary embodiments, the lipid base may include one of solid α-tocopherol succinate, triglycerides, partial glycerides, fatty acids, steroids, waxes, or combinations thereof.

In some exemplary embodiments, the α-tocopherol succinate may be used as an antibiotic carrier to enhance the drug permeation through the skin. In an exemplary embodiment, the triglycerides may include tri-stearin. In an exemplary embodiment, the fatty acids may include one of stearic acid, palmitic acid, or combinations thereof. In an exemplary embodiment, the steroids may include cholesterol. In an exemplary embodiment, the waxes may include cetyl palmitate.

In some exemplary embodiments, the oil phase may include the surfactant with a concentration between about 10% and about 50% of the weight of the oil phase. In one or more exemplary embodiments, the surfactant may include one of an ionic surfactant, a non-ionic surfactant, an amphiphilic surfactant, or combinations thereof. In one or more exemplary embodiments, the ionic surfactant may include one of alkyl phosphates, alkyl sulfates, or combinations thereof. In one or more exemplary embodiments, the non-ionic surfactant may include one of polyol esters, polyoxyethylene esters, poloxamers, or combinations thereof. In one or more exemplary embodiments, the Amphiphilic surfactant may include one of soybean phosphatidylcholine, egg phosphatidylcholine, synthetic phosphatidylcholine, hydrogenated phosphatidylcholine, or combinations thereof.

In some exemplary embodiments, the oil phase may include the cosurfactant with a concentration between about 1% and about 5% of the weight of the oil phase. In one or more exemplary embodiments, the cosurfactant may include one of an ionic cosurfactant, a non-ionic cosurfactant, an amphiphilic cosurfactant, or combinations thereof.

In one or more exemplary embodiments, the ionic cosurfactant may include one of alkyl phosphates, alkyl sulfates, or combinations thereof. In one or more exemplary embodiments, the non-ionic cosurfactant may include one of polyol esters, polyoxyethylene esters, poloxamers, or combinations thereof. In one or more exemplary embodiments, the amphiphilic cosurfactant may include one of soybean phosphatidylcholine, egg phosphatidylcholine, synthetic phosphatidylcholine, hydrogenated phosphatidylcholine, or combinations thereof.

In one or more exemplary embodiments, the zeta potential adjusting salt may include a stabilizer. In an exemplary embodiment, the stabilizer may include one of sodium citrate, cetyltrimethylammonium bromide (CTAB), polyvinylpyrrolidone (PVP), or combinations thereof. In some exemplary embodiments, the oil phase may include the zeta potential adjusting salt with a concentration between less than about 3% of the weight of the oil phase.

Step 112 may include forming the nanoemulsion including the antibiotic-loaded lipid nanoparticles by adding the oil phase to the aqueous phase. In one or more exemplary embodiments, the aqueous phase may include deionized water with a temperature of the oil phase between about 70° C. and about 80° C. In an exemplary implementation, the nanoemulsion containing antibiotic-loaded lipid nanoparticles may be formed by adding the oil phase to the aqueous phase and agitating to obtain a homogenous nanoemulsion.

Step 114 may include forming the nanosuspension including the plurality of antibiotic-loaded SLNs by adding cold deionized water to the nanoemulsion. In one or more exemplary embodiments, the nanosuspension containing antibiotic-loaded SLNs may be formed by adding cold deionized water with a temperature between about 4° C. and about 8° C. to the nanoemulsion while stirring for a time period of about 20 minutes.

In one or more exemplary embodiments, the nanosuspension including the SLNs may be further centrifuged at a speed of about 9000 RPM at a temperature of about 4° C. to precipitate the antibiotic-loaded SLNs. In some exemplary embodiments, the plurality of antibiotic-loaded SLNs may have a diameter between 90 nm and 180 nm. In some exemplary embodiments, the plurality of antibiotic-loaded SLNs may include an antibiotic entrapped inside the lipid matrix of the SLNs.

Referring back to method 100, step 106 may include forming the patch formulation by mixing the plurality of antibiotic-loaded SLNs and the polymeric adhesive solution. In some exemplary embodiments, the polymeric adhesive solution may be present in the patch formulation with a concentration of at least about 80% of the weight of the patch formulation. In some exemplary embodiments, the plurality of antibiotic-loaded SLNs may be present in the patch formulation with a concentration between about 3% and about 13% of the weight of the patch formulation. In some exemplary embodiments, the plurality of antibiotic-loaded SLNs may be present in the patch formulation with a concentration more than about 7% of the weight of the patch formulation In some exemplary embodiments, mixing the plurality of antibiotic-loaded SLNs and the polymeric adhesive solution may be done using a rotatory mixer or mechanical shaker with a speed between about 100 RPM and about 200 RPM. In some exemplary embodiments, mixing the plurality of antibiotic-loaded SLNs and the polymeric adhesive solution may be done overnight at room temperature until a homogeneous patch formulation is obtained.

In some exemplary embodiments, the patch formulation may further include a penetration enhancer. In an exemplary embodiment, the penetration enhancer may include one of water, hydrocarbons, alcohols, amino acids, amides, esters, terpene surface activators, base oils, sulfonic acids, lipids, cyclodextrin derivatives, chitosan derivatives, nanoparticles, or combinations thereof. In an exemplary embodiment, the penetration enhancer may include one of blank SLNs, oleic acid, or combinations thereof.

In some exemplary embodiments, the penetration enhancer may be present in the patch formulation with a concentration less than about 10% of the weight of the patch formulation. In some exemplary embodiments, the patch formulation may further include free antibiotics. In some exemplary embodiments, the free antibiotic may be present in the patch formulation with a concentration between about 7% and about 10% of the weight of the patch formulation.

Step 108 may include forming the layer of the patch formulation on the substrate. In some exemplary embodiments, forming the layer of the patch formulation on the substrate may include forming the layer of the patch formulation on the substrate using one of wire wound rod coating, knife-over-roll (KOR) coating, reverse-roll coating, extrusion slot die coating, slot die coating, curtain coating, or combinations thereof.

In some exemplary embodiments, forming the layer of the patch formulation on the substrate may include using a film applicator. In some exemplary embodiments, forming the layer of the patch formulation on the substrate may include forming the layer of the patch formulation on the substrate with a uniform thickness between about 60 μm and about 140 μm. In some exemplary embodiments, the layer of the patch formulation may have a uniform thickness between about 120 nm and about 130 nm on the substrate In some exemplary embodiments, the substrate may be a backing layer and may include one of polyethylene terephthalate (PET), polyolefins, high-density polyethylene (HDPE), low-density polyethylene (LDPE), polypropylene (PP), polyurethanes (PU), polyether amides (PEA), ethylene vinyl acetate (EVA), or combinations thereof. In some exemplary embodiments, the layer of the patch formulation on the substrate may be dried at room temperature for a time period between about 20 minutes and about 30 minutes. In some exemplary embodiments, a residual solvent of the layer of the patch formulation may be removed using an oven at a temperature of about 60° C. for a time period of about 1 hour.

Figure 2:
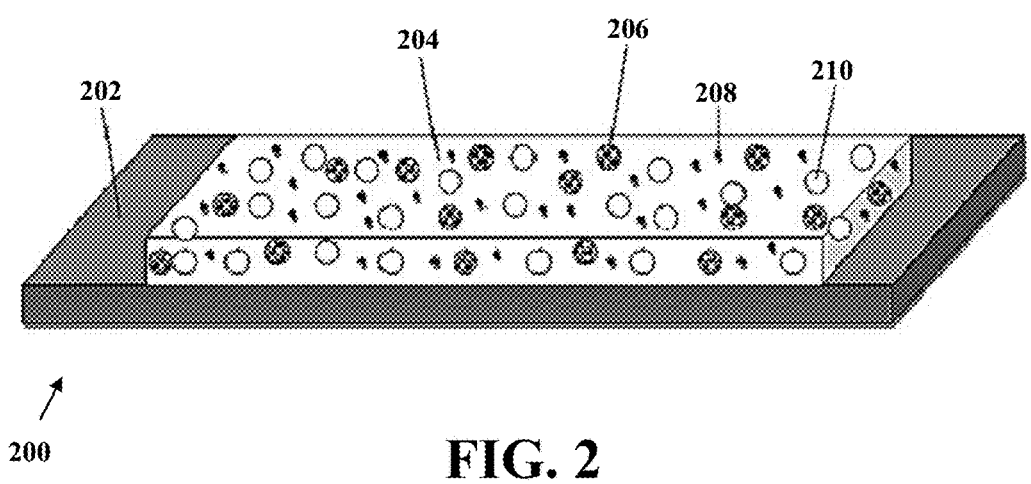
FIG. 2 illustrates a schematic view of an antibiotic-loaded transdermal patch, consistent with one or more exemplary embodiments of the present disclosure.

FIG. 2 shows a schematic view of antibiotic-loaded transdermal patch 200, consistent with one or more exemplary embodiments of the present disclosure. Referring to FIG. 2, antibiotic-loaded transdermal patch 200 may include layer of the patch formulation 204 coated on substrate 202. Layer of the patch formulation 204 may include plurality of antibiotic-loaded SLNs 206, free antibiotic 208, and penetration enhancer 210 which may be dispersed in the adhesive matrix of layer of the patch formulation 204. In some exemplary embodiments, plurality of antibiotic-loaded SLNs 206 may have a concentration between about 3% and about 13% of weight of the patch formulation.

In some exemplary embodiments, plurality of antibiotic-loaded SLNs 206 may include an antibiotic entrapped inside the lipid matrix of the SLNs. In some exemplary embodiments, free antibiotic 208 may have a concentration between about 7% and about 10% of the weight of the patch formulation. In some exemplary embodiments, penetration enhancer 210 may have a concentration less than about 10% of the weight of the patch formulation. In some exemplary embodiments, layer of the patch formulation 204 may have a uniform thickness between about 60 nm and about 140 nm.

In some exemplary embodiments, presence of penetration enhancer 210 in antibiotic-loaded transdermal patch 200 may increase the release and penetration of the antibiotic into skin about 3 times and may decrease 30% of the amount of required antibiotic compared to antibiotic-loaded transdermal patches without penetration enhancers. In one or more exemplary embodiments, layer of the patch formulation 204 may be adapted for contact with the skin. In some exemplary implementations, antibiotic-loaded transdermal patch 200 may increase skin cell proliferation and may be used for antibiotic prophylaxis treatments of the surgery wounds. Therefore, using antibiotic-loaded transdermal patch 200 may aid in decreasing antibiotic usage.

In some exemplary embodiments, antibiotic-loaded transdermal patch 200 may have a tack value between about 1.2 N/mm$^2$ and about 3.8 N/mm$^2$. In some exemplary embodiments, antibiotic-loaded transdermal patch 200 may have a peel value between about 8.5 N/25 mm and about 9.5 N/25 mm. In some exemplary embodiments, antibiotic-loaded transdermal patch 200 may have a mean maximum shear strength value between about 4 minutes and about 10 minutes.

EXAMPLES

Example 1: Preparation of the Cephalexin-Loaded Transdermal Patch

In this example, an exemplary cephalexin-loaded transdermal patch was prepared using exemplary steps of preparing a polymeric adhesive solution by dissolving a polymeric mixture in a solvent, preparing a plurality of antibiotic-loaded solid lipid nanoparticle (SLNs), forming a patch formulation by mixing the plurality of antibiotic-loaded SLNs and the polymeric adhesive solution, and forming a layer of the patch formulation on a substrate.

At first, the polymeric adhesive solution was prepared by dissolving a mixture of polyisobutylenes (PIBs) with different molecular weights in toluene using a rotary mixer at room temperature overnight. The polymeric adhesive solution was then obtained when PIBs were completely dissolved in toluene and the adhesive solution was visually homogeneous.

TABLE. 1 represents the composition of different PIB mixtures for preparing polymeric adhesive solutions. The mixture of PIBs included at least one low-molecular-weight (LMW) polymer such as PIB-B10, PIB-B12, and PIB-B15 polymers and at least one high-molecular-weight (HMW) polymer such as PIB-B50 and PIB-B100 polymers. The mixture of PIBs included the LMW polymer and the HMW polymer with a ratio between 70:30 and 60:40 (LMW polymer weight percent: HMW polymer weight percent).

TABLE 1

Composition of different PIB mixtures for preparing the polymeric adhesive solution

| Sample | B10 % | B12 % | B15 % | B50 % | B100 % |
|---|---|---|---|---|---|
| 1 | 0 | 0 | 60 | 0 | 40 |
| 2 | 0 | 0 | 60 | 40 | 0 |
| 3 | 0 | 0 | 70 | 0 | 30 |
| 4 | 0 | 70 | 0 | 0 | 30 |
| 5 | 70 | 0 | 0 | 0 | 30 |
| 6 | 60 | 0 | 0 | 40 | 0 |

In the next step, a plurality of cephalexin-loaded SLNs were prepared using O/W method. At first, an oil phase was prepared using a mixture of solid α-tocopherol succinate with an amount of about 200 mg as the lipid base, cephalexin as the antibiotic drug with an amount of about 40 mg, polysorbate 80 as the surfactant with an amount of about 1.32 gram, lecithin as the cosurfactant with an amount of about 20 mg, and sodium citrate as the zeta potential adjusting salt with an amount of about 20 mg. The mixture was heated to a temperature of about 76° C. as a melting point of lipids while stirring using a mechanical agitator at a speed of about 2000 RPM for a time period of about 10 minutes to obtain a homogeneous oil phase.

After preparing the oil phase, a nanoemulsion including lipid nanoparticles was formed by adding the oil phase to 1 ml of deionized water as an aqueous phase with the same temperature of the oil phase of about 76° C. The formed nanoemulsion was agitated at a speed of about 2000 RPM for a time period of about 10 min at a temperature of about 76° C. to obtain a homogenous nanoemulsion including the cephalexin-loaded lipid nanoparticles.

Afterward, a nanosuspension including cephalexin-loaded SLNs was formed by adding 10 ml of cold deionized water with a temperature of about 8° C. to the nanoemulsion while stirring for a time period about 20 minutes. In the end, the nanosuspension was centrifuged at a speed of about 9000 RPM at a temperature of about 4° C. to precipitate the cephalexin-loaded SLNs.

Figure 3:
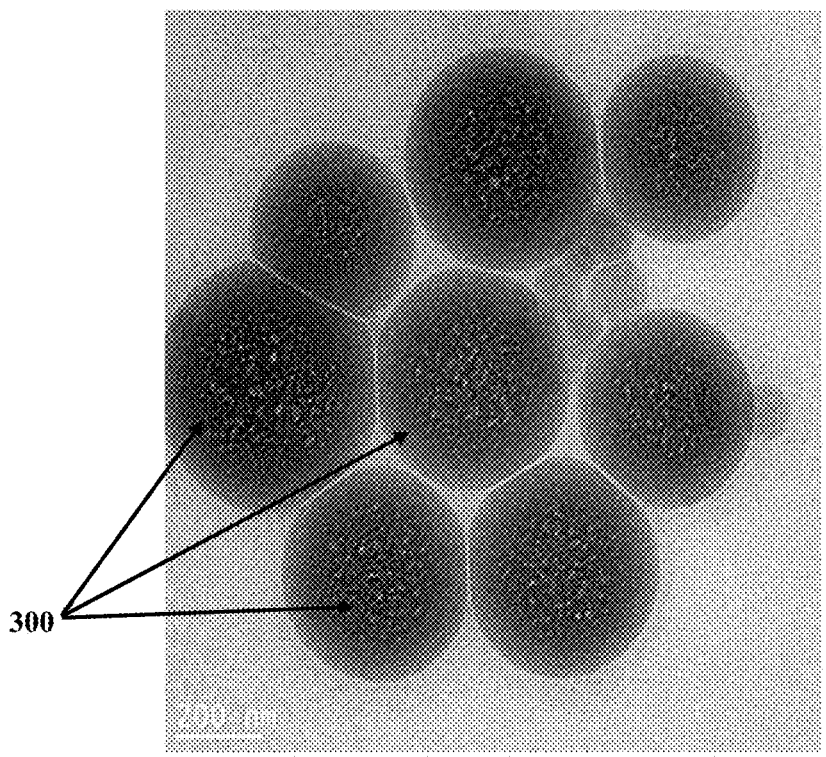
FIG. 3 illustrates a transmission electron microscope (TEM) image of cephalexin-loaded SLNs prepared by oil-in-water (O/W) method, consistent with one or more exemplary embodiments of the present disclosure.

Structure and surface morphology of the SLNs were determined using electron microscopy. FIG. 3 shows transmission electron microscopy (TEM) image of SLNs 300 prepared by O/W method, consistent with one or more exemplary embodiments of the present disclosure. Referring to FIG. 3, SLNs 300 had a spherical shape with a diameter between about 109 nm an about 120.

In the next step, patch formulation was formed by mixing the plurality of antibiotic-loaded SLNs and the polymeric adhesive solution using a rotary mixer at a speed of about 150 RPM and at room temperature overnight until a homogeneous patch formulation was obtained. The polymeric adhesive solution was present in the patch formulation with a concentration of about 80% of the weight of the patch formulation. The plurality of antibiotic-loaded SLNs was present in the patch formulation with a concentration about 10% of the weight of the patch formulation.

Moreover, the patch formulation further included a plurality of blank SLNs as the penetration enhancer with a concentration of about 3% of the weight of the patch formulation. The patch formulation further included free antibiotics with a concentration of about 7% of the weight of the patch formulation.

In the next step, the cephalexin-loaded transdermal patch was formed by forming the layer of the patch formulation on the substrate using a casting knife film applicator with a uniform thickness between about 120 nm and about 130 nm on the substrate. The substrate was a backing layer made up of ethylene vinyl acetate (EVA). Finally, the layer of the patch formulation was dried at room temperature for a time period of about 20 minutes, and a residual solvent of the layer of the patch formulation was removed using an oven at a temperature of about 60° C. for a time period of about 1 hour.

Figure 4:
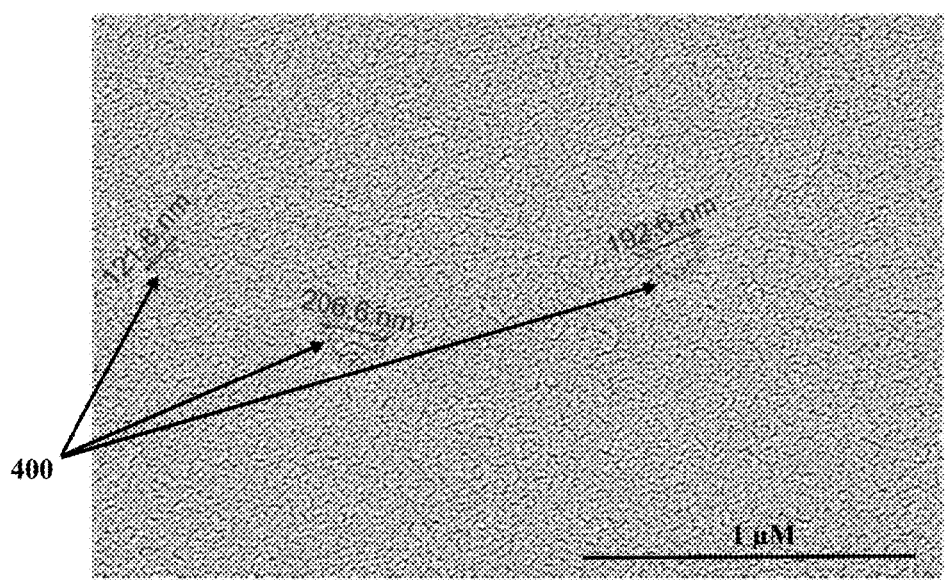
FIG. 4 illustrates transmission electron microscope (TEM) image of cephalexin-loaded SLNs in a cephalexin-loaded transdermal patch, consistent with one or more exemplary embodiments of the present disclosure.

FIG. 4 illustrates transmission electron microscope (TEM) image of cephalexin-loaded SLNs dispersed within an adhesive matrix of an antibiotic-loaded transdermal patch, consistent with one or more exemplary embodiments of the present disclosure. Referring to FIG. 4, cephalexin-loaded SLNs 400 are uniformly dispersed within an adhesive matrix of an antibiotic-loaded transdermal patch and have a mean diameter of about 182.6 nm.

Figure 5:
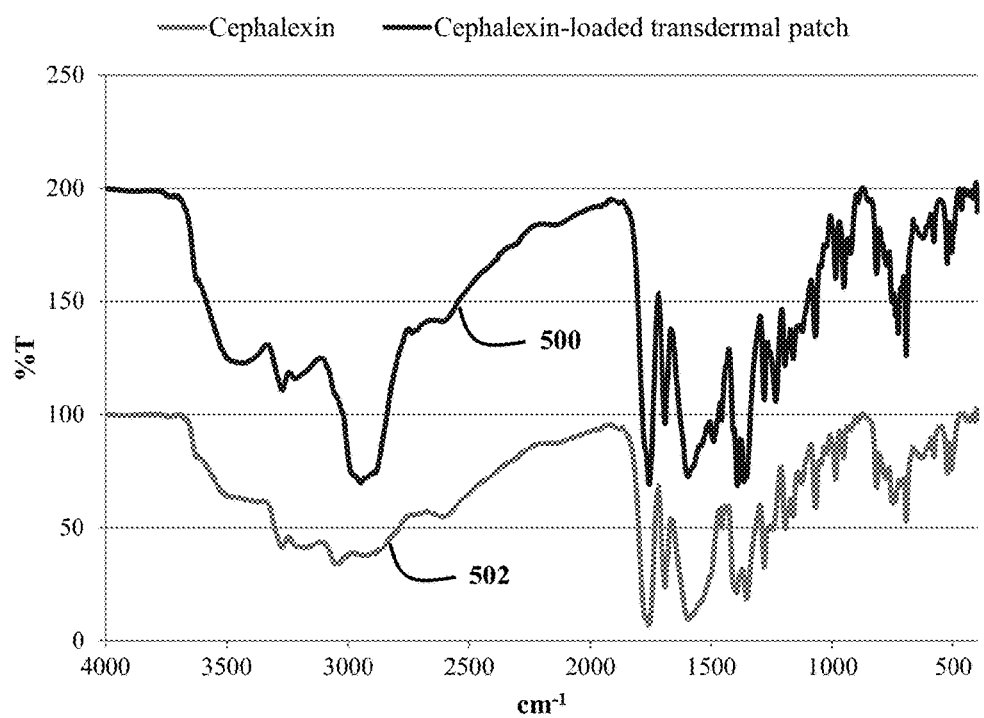
FIG. 5 shows Fourier transform infrared spectrometer (FT-IR) spectra of cephalexin and a cephalexin-loaded transdermal patch, consistent with one or more exemplary embodiments of the present disclosure.

FIG. 5 shows Fourier transform infrared spectrometer (FT-IR) spectra of cephalexin-loaded transdermal patch 500 and cephalexin 502, consistent with one or more exemplary embodiments of the present disclosure. Referring to FIG. 5, spectrum of the cephalexin-loaded transdermal patch 500 shows all prominent peaks of cephalexin spectrum 502, such as a peak at a wavelength of about 3273 (3100-3500) for N—H bonds, a peak at a wavelength of about 1688.79 for C=O bonds, a peak at a wavelength of about 2606 for S—H bonds, a peak at a wavelength of about 1143.26 for C—N bonds, and a peak at a wavelength of about 1281.46 for C—O bonds. Therefore, there was no interaction between cephalexin and other components in the cephalexin-loaded transdermal patch.

Example 2: Evaluation of Adhesive Properties of Adhesive Layers

In this example, adhesive properties such as tack, peel, and shear parameters and thermal analysis of different adhesive layers of the polymeric adhesive solutions of EXAMPLE 1 were determined. Before conducting these tests, thermal analysis was used to show that the adhesive polymers have been completely dissolved in the solvent.

At first, tack test was carried out according to ASTM-D3121 for at least five times for each sample of the layer of the patch formulation. Tack is the ability of a layer of the patch formulation to stick to a substrate under low pressure and to be removed by adhesive separation. A stripe of the layer of the patch formulation with about 2.5 cm width and about 2.5 cm length was coated on the standard steel panel of tack instrument. The probe of tack instrument with a rate of about 10±0.1 mm/s was adhered to the center of stripe and separated with the same rate. In the end, the tack of the PS layer was determined as the maximum force to separate 1 mm² of adhesive from the probe tack.

Also, a peel test was carried out according to the ASTM-D3330 on strips of the layer of the patch formulation with about 25 mm width and about 30 cm length. Dried strips of the layer of the patch formulation were pressed in stainless steel plate by 5 kg rubber roller passing two times over the sample. Then, the adhesive/stainless steel joints were stored at room temperature for a time period of about 20 minutes. In the end, the peel force at an angle of about 180° direction was measured at a peel rate of about 30 cm/min.

Moreover, the shear test was carried out according to ASTM-D3654. A strip of the layer of the patch formulation with about 12 cm width and about 12 cm length was coated on a standard steel panel under 5 kg rubber roller passing, and the panel was mounted vertically on a shear test instrument. A standard weight of about 0.5 kg was attached to the free end of the tape, and the time to failure was determined as shear adhesion measurement. TABLE. 2 represents adhesive properties such as tack, peel, and shear of different adhesive layers with different formulations.

TABLE 2

Adhesive properties of different layers of the patch formulation s

| Sample | B10 | B12 | B15 | B50 | B100 | Tack (N/mm²) | Peel (N/25 mm) | Shear (min) |
|---|---|---|---|---|---|---|---|---|
| 1 | 0 | 0 | 60 | 0 | 40 | 1.49 | 2.85 | 19.5 |
| 2 | 0 | 0 | 60 | 40 | 0 | 1.38 | 3.10 | 22.8 |
| 3 | 0 | 0 | 70 | 0 | 30 | 1.62 | 2.18 | 43.5 |
| 4 | 0 | 70 | 0 | 0 | 30 | 1.69 | 8.08 | 8.9 |
| 5 | 70 | 0 | 0 | 0 | 30 | 2.25 | 6.35 | 6.45 |
| 6 | 60 | 0 | 0 | 40 | 0 | 3.4 | 15.87 | 4.73 |

Referring to TABLE. 2, the adhesive layers had a mean tack value between about 1.2 N/mm² and about 3.8 N/mm²' and an optimum tack value between about 2.8 N/mm² and about 3.5 N/mm² was observed for the adhesive layer including B10 and B50 polymers. Also, the adhesive layer had a mean peel value between about 2 N/25 mm and about 16 N/25 mm, and an optimum peel value between about 13.5 N/25 mm and about 16 N/25 mm was observed for adhesive layer including B10 and B50 polymers. Moreover, the adhesive layer had a mean shear strength value between about 2 minutes and about 45 minutes, and an optimum shear strength value was observed for the adhesive layer including B10 and B50 polymers.

Example 3: Characterization of Solid Lipid Nanoparticles (SLNs)

In this example, the solid lipid nanoparticles (SLNs) which were prepared by utilizing two methods in EXAMPLE 1 were characterized by determining drug content, particle size, loading capacity (LC), and zeta potential of the SLNs. In order to characterize SLNs, they were dried in a lyophilizer. The supernatant was recovered and carefully filtered using a membrane with a filter mesh of about 0.22 µm.

High-performance liquid chromatography (HPLC) analysis was used to quantify drug content in SLNs. Also, particle size, polydispersity index (PI), and zeta potential as an indicator of surface charge of the SLNs were evaluated by dynamic light scattering (DLS). Solid lipid nanoparticle (SLN) loading capacity was evaluated by HPLC analysis of drug content in the supernatant.

Also, the in-vitro release of cephalexin from SLNs was evaluated using dialysis bag with a molecular weight (MW) cut off about 12000 kiloDalton (kDa). The specified amount of cephalexin-loaded SLNs was transferred to a dialysis bag which was placed in a beaker containing buffer phosphate with a pH level of about 7.4 at a temperature of about ° C.

At predetermined time intervals during 24 hours, the entire buffer phosphate solution of the beaker was taken and replaced with fresh medium. The concentration of cephalexin in the buffer phosphate solution of the beaker was determined by HPLC at each defined time, and the loading capacity (LC) was calculated by Eq. 1, where $M_{initial\ drug}$ is the mass of initial drug used for preparing SLNs, $M_{free\ drug}$ is the mass of free drug detected in the supernatant, and $M_{SLN}$ is the mass of obtained SLNs.

$$LC\% = \frac{M_{initial\ drug} - M_{free\ drug}}{M_{SLN}} \times 100 \qquad \text{Eq. 1}$$

The SLNs prepared by O/W and W/O methods have different inner structures that causes different properties. TABLE. 3 represents different characteristics of the SLNs which were prepared using one of O/W method or W/O method.

TABLE 3

Characteristics of SLNs prepared by O/W or W/O methods

| Method | (Drug/Lipid) % | Size (nm) | Zeta potential (mV) | Loading Capacity % |
|---|---|---|---|---|
| O/W | 20 | 182 ± 7.1 | −7.8 ± 0.2 | 7.88 |
| W/O | 20 | 114.5 ± 5.3 | −13.1 ± 0.4 | 6.7 |

Referring to TABLE. 3, the results indicate that the SLNs prepared by W/O method had a smaller size than the SLNs prepared by O/W method. While zeta potential of SLNs prepared by W/O method was more negative than the SLNs prepared by O/W method, the SLNs prepared by W/O method was more stable. However, the loading capacity (LC %) of SLNs prepared by O/W method was more than LC % of SLNs prepared by W/O method due to their bigger size.

Example 4: Antibacterial Activity of the Antibiotic-Loaded Transdermal Patch and its Component

*Staphylococcus aureus* is the microorganism that is most existent on the surface of the skin causing infections in surgery suture places. In this example, antibacterial activities of a cephalexin-loaded transdermal patch and SLNs were investigated against *Staphylococcus aureus* as gram-positive bacteria by disk diffusion method. In the disk diffusion method, inhibition zone diameter was measured to determine the antibacterial activity of different formulations.

At first, *Staphylococcus aureus* bacteria were incubated in Luria-Bertani broth medium overnight at a temperature of about 37° C. and then diluted with sterile water to obtain a bacterial solution suspension a density of about $10^6$ cells/ml.

The bacterial suspension was then plated by the spread plate method on nutrient agar in duplicate.

In order to determine antibacterial activity of cephalexin-loaded SLNs, about 5 mg of cephalexin-loaded SLNs prepared by two methods of O/W and W/O in EXAMPLE 1 was placed on the surface of nutrient agar inoculated with bacterial suspension, and incubated overnight at a temperature of about 37° C. After that, clear area around each sample was determined as a zone of inhibition and measured by Image J-1.49V software.

According to the results, the inhibition zone diameter of the cephalexin-loaded SLNs prepared by the O/W method was between about 39 mm and about 43 mm, and the inhibition zone diameter of the cephalexin-loaded SLNs prepared by the W/O method was between about 34 mm and 36 mm. Therefore, the cephalexin-loaded SLNs prepared by the O/W method have more killing ability than the cephalexin-loaded SLNs prepared by the W/O method. While the cephalexin-loaded SLNs prepared by the O/W method have a higher loading capacity and a higher inhibitory effect, it can be concluded that there is a direct relationship between loading capacity and the inhibitory effect of the cephalexin-loaded SLNs.

Moreover, in order to determine antibacterial activity of the cephalexin-loaded transdermal patches with different formulations, the strip of patches with an area of about 0.7 $cm^2$ was placed on nutrition agar plates covered by *Staphylococcus aureus* microorganism and incubated overnight at a temperature of about 37° C. Then, the clear area around each strip was determined as a zone of inhibition and measured by software.

TABLE. 4 represents inhibition zone diameter of cephalexin-loaded transdermal patches with different concentrations of cephalexin and SLNs. Referring to TABLE. 4, the cephalexin-loaded transdermal patch including about 7% cephalexin and about 3% SLNs showed inhibition zone diameter of about 19.9, while the transdermal patch including 10% cephalexin without any SLN showed inhibition zone diameter of about 20.3.

Therefore, addition of the SLNs into a cephalexin-loaded transdermal patch did not significantly decrease the antibacterial activity of the transdermal patch. Moreover, the cephalexin-loaded transdermal patch including SLNs showed the same antibacterial activity with 30% lower amount of cephalexin. It can be concluded that presence of the SLNs in the cephalexin-loaded transdermal patch protects the cephalexin from hydrolysis while it works as a permeation enhancer. Therefore, presence of SLNs in the cephalexin-loaded transdermal patch leads to use lower amount of cephalexin without any change in the therapeutic effect of the transdermal patch.

TABLE 4

Inhibition zone diameter of cephalexin-loaded transdermal patches with different formulations

| Run | Adhesive polymers (% wt) | Cephalexin (% wt) | Cephalexin-loaded SLNs (% wt) | Inhibition zone diameter (mm) |
|---|---|---|---|---|
| 1 | 90 | 10 | 0 | 20.3 |
| 2 | 90 | 9 | 1 | 16.5 |
| 3 | 90 | 7 | 3 | 19.9 |
| 4 | 90 | 5 | 5 | 17.1 |
| 5 | 90 | 0 | 10 | 0.5 |

TABLE. 5 represents initial composition and inhibition zone diameter for three formulations of the cephalexin-loaded transdermal patch after 24 hours. Referring to TABLE. 5, the inhibition zone diameter for formulation with 10% blank-SLNs shows that the SLNs increased the antibacterial effect of the cephalexin-loaded transdermal patch. Therefore, using SLNs in the structure of the cephalexin-loaded transdermal patch enhanced antibacterial effects of the cephalexin-loaded transdermal patch.

TABLE 5

Initial composition and inhibition zone diameter for three formulations of the cephalexin-loaded transdermal patch after 24 hours

| Formulation | Drug (% wt) | Adhesive polymers (% wt) | Blank-SLNs (wt %) | Oleic acid (% wt) | Inhibition zone diameter (mm) |
|---|---|---|---|---|---|
| 1 | 10 | 90 | 0 | 0 | 20.3 ± 0.6 |
| 2 | 10 | 80 | 0 | 10 | 20.9 ± 0.3 |
| 3 | 10 | 80 | 10 | 0 | 27.5 ± 0.4 |

Example 5: Effect of Penetration Enhancers in the Cephalexin-Loaded Transdermal Patch In this example, in-vitro release studies of cephalexin from cephalexin-loaded transdermal patches in the presence and absence of different permeation enhancers were conducted in the Chien-type diffusion cells using the skin of two-month male rats. In order to determine the effect of SLNs as a permeation enhancer in the formulation of the cephalexin-loaded transdermal patch, different formulations of the cephalexin-loaded transdermal patch containing 0 to 10% blank-SLNs and 0 to 10% oleic acid as chemical permeation enhancer was prepared.

At first, whole skin of a two-month male rat between about 150 grams and 170 grams in weight was excised after the slaughter of animals in a local slaughterhouse. Nerves, blood vessels, hairs, and the adipose tissue layer were removed with the aid of a surgical scalpel and scissors. After that, each Chien diffusion cell with an effective diffusion area of about 1.13 $cm^2$ was filled with about 3 mL of a receptor medium containing phosphate buffer with pH of about 7.4. Then, receptor medium was stirred with a constant speed of about 100 RPM at a temperature of about 37° C. using a circulating water bath.

In the next step, strips of cephalexin-loaded transdermal patches with different percentages of permeation enhancers and with the area of about 2.25 $cm^2$ were directly placed over rat skin in the receptor medium, and at predetermined time intervals of 30 minutes, 1 hours, 2 hours, 4 hours, 8 hours, 12 hours, and 24 hours, the entire phosphate buffer of the receptor medium was taken and replaced with an equal volume of the fresh receptor medium. In the end, cumulative drug release from rat skin was calculated during 24 hours using HPLC analysis. TABLE. 6 represents initial composition and cumulative drug release for three formulations of the cephalexin-loaded transdermal patch after 24 hours.

TABLE 6

Comparison the effects of blank SLNs and oleic acid in the cephalexin-loaded transdermal patch as penetration enhancers

| Formulation | Drug (% wt) | Adhesive polymers (% wt) | Blank SLNs (wt %) | Oleic acid (% wt) | Cumulative drug release (µg/cm$^2$) |
|---|---|---|---|---|---|
| 1 | 10 | 90 | 0 | 0 | 202 ± 35 |
| 2 | 10 | 80 | 0 | 10 | 229 ± 48 |
| 3 | 10 | 80 | 10 | 0 | 612 ± 18 |

Figure 6:
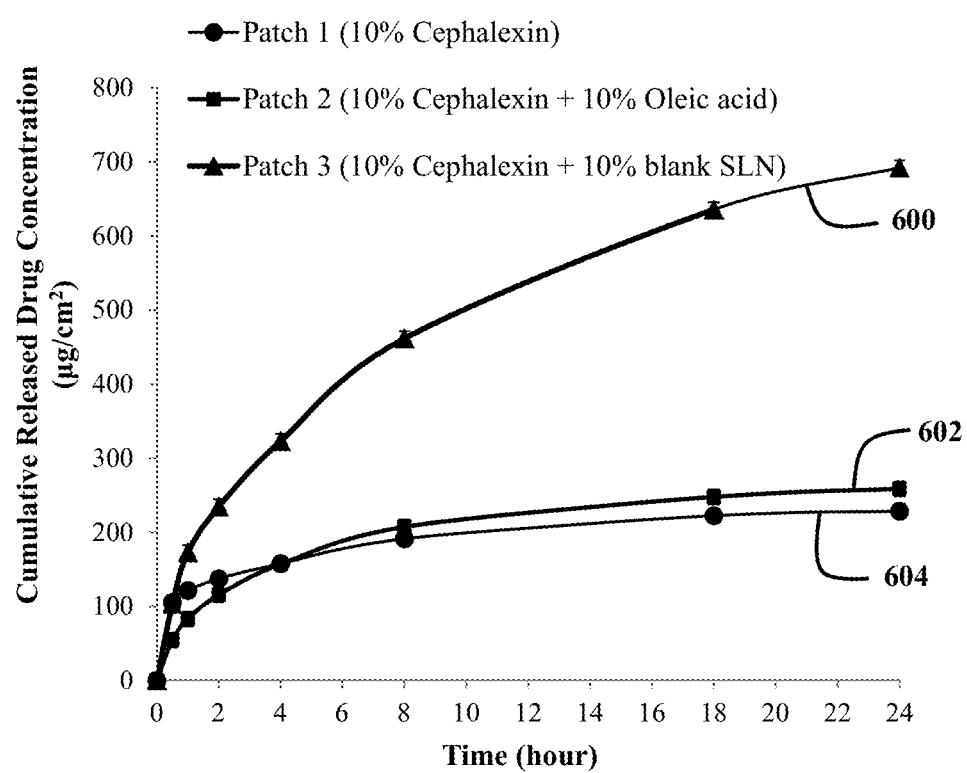
FIG. 6 illustrates a graph of cumulative drug release for three cephalexin-loaded transdermal patches during 24 hours, consistent with one or more exemplary embodiments of the present disclosure.

FIG. 6 shows a graph of cumulative drug release for three formulations of the cephalexin-loaded transdermal patch during 24 hours, consistent with one or more exemplary embodiments of the present disclosure. Referring to FIG. 6, comparison between graph 604 of patch 1 containing only 10% cephalexin and graph 600 of patch 3 containing 10% cephalexin and 10% blank SLNs indicates that presence of the blank SLNs led to release of the cephalexin in a sustained manner during 8 hours from the cephalexin-loaded transdermal patch.

Referring to FIG. 6 and TABLE. 6, comparison between graph 600 of patch 3 containing only 10% cephalexin and 10% blank SLNs and graph 602 of patch 2 containing 10% cephalexin and 10% oleic acid indicates that substitution of 10% wt SLNs for 10% wt oleic acid increased cephalexin release about 3 times.

The presence of SLNs on the skin causes to improve the hydration of skin and decrease the membrane properties of stratum corneum layer of the epidermis. In addition, the presence of surfactants such as polysorbate 80 in the formulation of SLNs facilitates penetration of the cephalexin through the skin. Therefore, SLN was a better permeation enhancer in comparison with oleic acid as a common chemical permeation enhancer.

Example 6: In-Vitro Release of the Antibiotic from the Antibiotic-Loaded Transdermal Patch In this example, amount of the released cephalexin from the cephalexin-loaded transdermal patch during 24 hours was compared with the minimum inhibitory concentration (MIC) of the cephalexin for *Staphylococcus aureus*. The cephalexin-loaded transdermal patch included 10% cephalexin-loaded SLNs, 7% free cephalexin, and 3% blank SLNs as the penetration enhancer.

Figure 7:
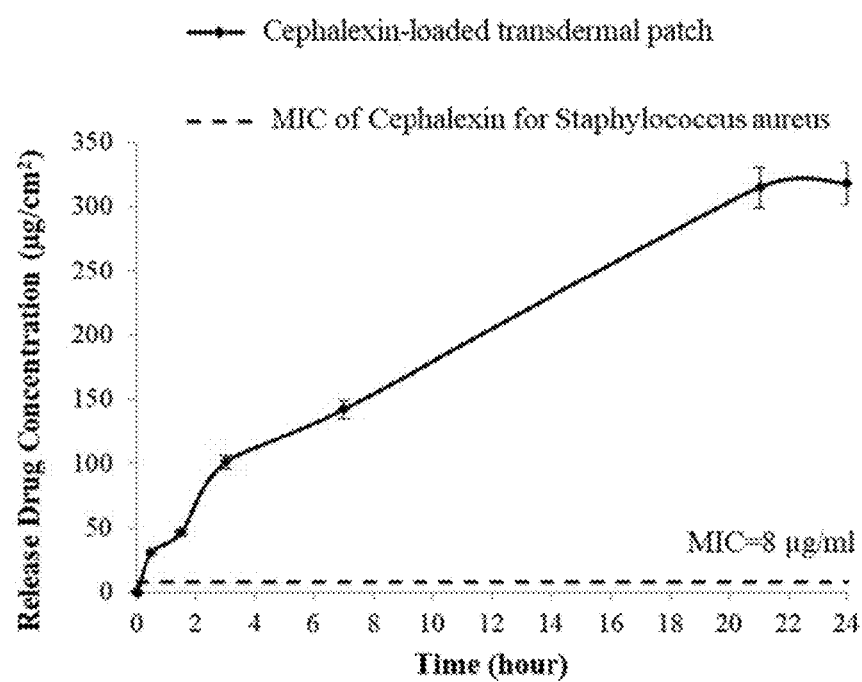
FIG. 7 illustrates a graph of cephalexin release from a cephalexin-loaded transdermal patch during 24 hours, consistent with one or more exemplary embodiments of the present disclosure.

FIG. 7 illustrates a graph of cephalexin release from the cephalexin-loaded transdermal patch during 24 hours, consistent with one or more exemplary embodiments of the present disclosure. Referring to FIG. 7, the amount of the released cephalexin from the cephalexin-loaded transdermal patch was always higher than the MIC of the cephalexin for *Staphylococcus aureus* which is about 8 µg/ml. Therefore, the cephalexin-loaded transdermal patch may have an acceptable antibacterial activity by releasing required amount of the cephalexin.

Example 7: Effects of the Cephalexin-Loaded Transdermal Patch on Growth Rate of Skin Cells In this example, effects of the cephalexin-loaded transdermal patch on the growth rate of skin cells were determined using cell proliferation techniques. In this technique Alamar-blue cell viability assay was conducted at days 1 and 4 of seeding human skin cells on a cephalexin-loaded transdermal patch.

At first, the Alamar-blue reagent was added to each well of a 48-well plate containing the cephalexin-loaded transdermal patch with seeded skin cells with a volume of about 10% of the culture medium 7 hours before each measurement. After incubation of the Alamar-blue reagent with the skin cells, about 200 µl of each sample was taken in triplicate and optical density (OD) of each sample at a wavelength of about 570 nm and 600 nm was measured. Finally, in order to determine the cellular proliferation of each sample, the percentage of the Alamar-blue reduction in each well was calculated using the OD results.

Figure 8:
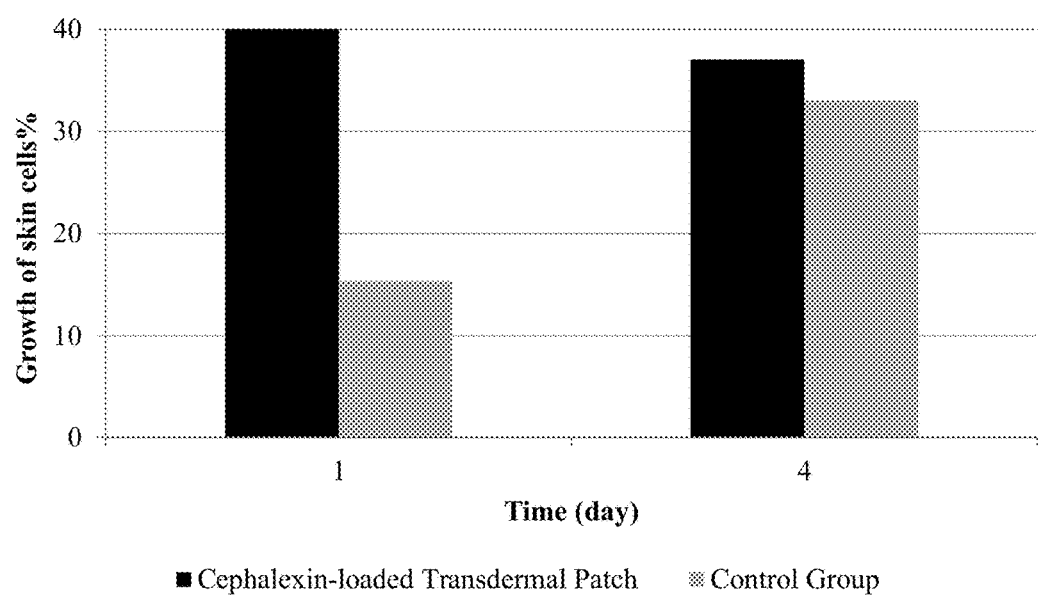
FIG. 8 illustrates growth rates of skin cells in the presence or absence of a cephalexin-loaded transdermal patch, consistent with one or more exemplary embodiments of the present disclosure.

FIG. 8 shows growth rates of skin cells in the presence or absence of the cephalexin-loaded transdermal patch, consistent with one or more exemplary embodiments of the present disclosure. Referring to FIG. 8, the results indicate that the exemplary cephalexin-loaded transdermal patch led to increasing the growth of human skin cells during 4 days. During the first day, the human skin cells grew 41% in the test group with the presence of the cephalexin-loaded transdermal patch and 15.37% in the control group. Therefore, the presence of SLNs containing α-tocopherol succinate could enhance cellular growth. Also, sustained release of the cephalexin in presence of the SLNs could increase the skin cell proliferation during 4 days.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in the light of the attached claims and their equivalents. Also, various modifications and changes may be made within the scope of the attached claims.

What is claimed is:

1. A method for producing an antibiotic-loaded transdermal patch, comprising:
   preparing a polymeric adhesive solution by dissolving a polymeric mixture in a solvent;
   preparing a plurality of antibiotic-loaded solid lipid nanoparticles (SLNs), the plurality of antibiotic-loaded SLNs comprising an antibiotic with a daily dose of at least 200 mg;
   forming a patch formulation by mixing a plurality of blank SLNs, the plurality of antibiotic-loaded SLNs, and the polymeric adhesive solution, the patch formulation comprising the plurality of blank SLNs with a concentration less than 10% of the weight of the patch formulation; and
   forming a layer of the patch formulation on a substrate.

2. The method according to claim 1, wherein the patch formulation comprises the plurality of antibiotic-loaded SLNs with a concentration between 3% and 13% of the weight of the patch formulation.

3. The method according to claim 1, wherein the patch formulation comprises free antibiotic with a concentration between 7% and 10% of the weight of the patch formulation.

4. The method according to claim 1, wherein the plurality of antibiotic-loaded SLNs further comprises a lipid base, a surfactant, a cosurfactant, zeta-potential adjusting salt, or combinations thereof.

5. The method according to claim 1, wherein the plurality of antibiotic-loaded SLNs comprises the antibiotic with a molar mass less than 500 g/mol.

6. The method according to claim 4, wherein the lipid base comprises one of solid α-tocopherol succinate, triglycerides, partial glycerides, fatty acids, steroids, waxes, or combinations thereof.

7. The method according to claim 1, wherein the plurality of antibiotic-loaded SLNs has a diameter between 90 nm and 180 nm.

8. The method according to claim 1, wherein the polymeric mixture further comprises at least one of acrylic-based polymers, and silicon-based polymers.

9. The method according to claim 1, wherein the layer of the patch formulation has a thickness between 60 μm and 140 μm.

10. An antibiotic-loaded transdermal patch, comprising:
    a layer of a patch formulation coated on a substrate, the patch formulation comprising:
      a polymeric adhesive solution comprising low-molecular-weight (LMW) polyisobutylene (PIB) and high-molecular-weight (HMW) PIB with a ratio of LMW PIB to HMW PIB between 70:30 and 60:40;
      a plurality of antibiotic-loaded solid lipid nanoparticles (SLNs) with a concentration between 3% and 10% of the weight of the patch formulation uniformly dispersed in the polymeric adhesive solution, the plurality of antibiotic-loaded SLNs comprising an antibiotic with a daily dose of at least 200 mg; and
      a plurality of blank SLNs with a concentration less than 10% of the weight of the patch formulation.

11. The antibiotic-loaded transdermal patch according to claim 10, wherein the patch formulation further comprises free antibiotic with a concentration between 7% and 10% of the weight of the patch formulation.

12. A method for producing an antibiotic-loaded transdermal patch, comprising:
    preparing a polymeric adhesive solution by dissolving a polymeric mixture in a solvent;
    preparing a plurality of antibiotic-loaded solid lipid nanoparticles (SLNs), the plurality of antibiotic-loaded SLNs comprising cephalexin with a daily dose of at least 200 mg;
    forming a patch formulation by mixing a plurality of blank SLNs, the plurality of antibiotic-loaded SLNs, and the polymeric adhesive solution, the patch formulation comprising the plurality of blank SLNs with a concentration less than 10% of the weight of the patch formulation; and
    forming a layer of the patch formulation on a substrate.

* * * * *